(12) United States Patent
Luotola (10) Patent No.: US 9,694,358 B2
(45) Date of Patent: Jul. 4, 2017

(54) SAMPLING AND DISPENSING DEVICE

(75) Inventor: Juhani Luotola, Espoo (FI)

(73) Assignee: ORION DIAGNOSTICA OY, Espoo (FI)

( * ) Notice: Subject to any disclaimer, the term of this patent is extended or adjusted under 35 U.S.C. 154(b) by 0 days.

(21) Appl. No.: 12/935,078

(22) PCT Filed: Mar. 27, 2009

(86) PCT No.: PCT/FI2009/000038
§ 371 (c)(1),
(2), (4) Date: Sep. 28, 2010

(87) PCT Pub. No.: WO2009/118444
PCT Pub. Date: Oct. 1, 2009

(65) Prior Publication Data
US 2011/0020195 A1    Jan. 27, 2011

Related U.S. Application Data

(60) Provisional application No. 61/040,428, filed on Mar. 28, 2008.

(51) Int. Cl.
*A61M 1/00* (2006.01)
*A61B 5/00* (2006.01)
(Continued)

(52) U.S. Cl.
CPC ...... *B01L 3/0282* (2013.01); *A61B 5/150022* (2013.01); *A61B 5/150213* (2013.01); *A61B 5/150236* (2013.01); *A61B 5/150244* (2013.01); *A61B 5/150251* (2013.01); *A61B 5/150343* (2013.01); *A61B 5/150351* (2013.01); *A61B 5/150755* (2013.01); *A61B 10/0045* (2013.01);
(Continued)

(58) Field of Classification Search
USPC ........ 600/573, 577, 578, 583, 584; 604/122; 422/512
See application file for complete search history.

(56) References Cited

U.S. PATENT DOCUMENTS 3,045,494 A   7/1962   Gerarde
3,233,785 A   2/1966   Burke
(Continued)

FOREIGN PATENT DOCUMENTS

CH    384899 A      2/1965
EP    0055859 A2    7/1982
(Continued)

OTHER PUBLICATIONS

Australia Patent Examination Report No. 1 regarding application No. 2009229000 issued Jul. 23, 2013.
(Continued)

*Primary Examiner* — Sean Dougherty
(74) *Attorney, Agent, or Firm* — Harness, Dickey & Pierce, P.L.C.

(57) ABSTRACT

The present invention relates to a device and method for easy collection, dilution, mixing and dispensing of a liquid specimen in a self-contained system. The present invention can be used in combination with numerous testing means for performing chemical, biochemical or biomedical qualitative or quantitative assays in the field of both clinical and hygiene testing.

55 Claims, 8 Drawing Sheets

(51) Int. Cl.
*B01L 1/00* (2006.01)
*B01L 3/02* (2006.01)
*A61B 10/00* (2006.01)
*A61B 5/15* (2006.01)
*A61J 1/20* (2006.01)
*A61M 5/28* (2006.01)

(52) U.S. Cl.
CPC ........... *B01L 3/022* (2013.01); *A61B 10/0051* (2013.01); *A61B 2010/0067* (2013.01); *A61J 1/2093* (2013.01); *A61M 5/283* (2013.01); *B01L 2300/044* (2013.01); *B01L 2300/0672* (2013.01); *B01L 2400/0406* (2013.01); *B01L 2400/0478* (2013.01)

(56) References Cited

U.S. PATENT DOCUMENTS

| | | | |
|---|---|---|---|
| 3,453,941 A | 7/1969 | Marachy | |
| 3,645,252 A * | 2/1972 | Gilford | 600/575 |
| 3,706,305 A * | 12/1972 | Berger et al. | 600/575 |
| 3,785,379 A * | 1/1974 | Cohen | 604/88 |
| 3,848,581 A | 11/1974 | Cinqualbre et al. | |
| 3,869,068 A | 3/1975 | Chen | |
| 3,901,765 A * | 8/1975 | Mehl | 435/34 |
| 4,003,262 A | 1/1977 | Gerarde et al. | |
| 4,050,451 A * | 9/1977 | Columbus | 600/577 |
| 4,091,802 A * | 5/1978 | Columbus | A61B 5/1405 210/516 |
| 4,133,304 A * | 1/1979 | Bailey | 600/577 |
| 4,134,300 A | 1/1979 | Svensson | |
| 4,136,036 A | 1/1979 | Columbus | |
| 4,192,320 A * | 3/1980 | Megahed | 600/577 |
| 4,396,024 A | 8/1983 | Sarstedt | |
| 4,449,539 A | 5/1984 | Sarstedt | |
| 4,589,421 A | 5/1986 | Ullman | |
| 4,690,005 A | 9/1987 | Tervamaki et al. | |
| 4,900,303 A * | 2/1990 | Lemelson | A61N 5/1014 604/11 |
| 4,936,830 A | 6/1990 | Verlier | |
| 4,976,925 A * | 12/1990 | Porcher et al. | 422/501 |
| 5,065,768 A * | 11/1991 | Coleman et al. | 600/573 |
| 5,066,280 A * | 11/1991 | Braithwaite | 604/110 |
| 5,181,523 A | 1/1993 | Wendelborn | |
| 5,215,102 A * | 6/1993 | Guirguis | B01L 3/502 422/401 |
| 5,339,830 A * | 8/1994 | Blake, III | 600/584 |
| 5,360,012 A * | 11/1994 | Ebara et al. | 600/577 |
| 5,456,885 A * | 10/1995 | Coleman et al. | 422/533 |
| 5,653,694 A * | 8/1997 | Powles et al. | 604/240 |
| 5,707,876 A * | 1/1998 | Levine | 436/177 |
| 5,833,630 A * | 11/1998 | Kloth | A61B 5/1411 604/508 |
| 5,935,864 A | 8/1999 | Schramm et al. | |
| 5,997,512 A * | 12/1999 | Shaw | 604/195 |
| 6,024,138 A | 2/2000 | Fritz et al. | |
| 6,126,618 A * | 10/2000 | Bischof | 600/576 |
| 6,196,979 B1 * | 3/2001 | Virtanen | 600/573 |
| 6,425,880 B1 * | 7/2002 | Marshall | 604/82 |
| 6,803,021 B1 | 10/2004 | Bertling | |
| 7,329,235 B2 * | 2/2008 | Bertron et al. | 604/88 |
| 7,503,907 B1 | 3/2009 | Lesch, Jr. | |
| 7,530,967 B2 * | 5/2009 | Brown | 604/122 |
| 7,896,818 B2 * | 3/2011 | Fremming et al. | 600/573 |
| 8,070,739 B2 * | 12/2011 | Zinger | A61J 1/2089 604/411 |
| 8,137,307 B2 * | 3/2012 | Tennican | A61M 5/31596 604/184 |
| 8,562,582 B2 * | 10/2013 | Tuckwell | A61J 1/2096 138/162 |
| 2005/0145046 A1 | 7/2005 | Blankenstein et al. | |
| 2005/0245885 A1 * | 11/2005 | Brown | 604/264 |
| 2006/0079834 A1 * | 4/2006 | Tennican | A61J 1/2096 604/88 |
| 2006/0175425 A1 * | 8/2006 | McGee | A01M 1/2033 239/44 |

FOREIGN PATENT DOCUMENTS

| | | |
|---|---|---|
| EP | 0872279 A2 | 10/1998 |
| GB | 2206800 A | 1/1989 |
| JP | 09113421 | 5/1997 |
| SU | 299053 | 3/1971 |
| WO | WO-79/01131 A1 | 12/1979 |
| WO | WO-00/13723 A2 | 3/2000 |
| WO | WO-01/30424 A1 | 5/2001 |
| WO | 2005071388 A1 | 8/2005 |
| WO | WO-2006/086291 A2 | 8/2006 |

OTHER PUBLICATIONS

International Preliminary Report on Patentability and Written Opinion regarding Application No. PCT/FI2009/000038 dated Jul. 16, 2009.
Japan Office Action regarding Application No. 2011-501255 dated Aug. 27, 2013.
Search Report regarding Application No. GB0806544.3 dated Aug. 8, 2008.
Office Action regarding Russian Application No. 2010144027/14(063450) dated Mar. 18, 2013. Translation provided by Gorodissky & Partners.
Decision on Grant regarding Russian Application No. 2010144027/14(063450) dated Oct. 17, 2013. Translation provided by Gorodissky & Partners.
Office Action from the European Patent Office regarding Application No. 09725660.6 dated Jan. 3, 2014.
Office Action issued by the European Patent Office on Sep. 17, 2015, regarding Application No. 09 725 660.6.
Office Action issued by the Canadian Intellectual Property Office on Aug. 24, 2015, regarding Application No. 2,719,813.
Summons to Attend Oral Proceedings regarding European Patent Application No. 09725660.6, dated Apr. 18, 2017.

* cited by examiner

SAMPLING AND DISPENSING DEVICE

The present invention relates to a device for dispensing a sample and method for dispensing samples to be analysed. The present invention also provides means for mixing a sample, reagent and a fluid stored in a sealed chamber in addition to a volumetric dispensing of the sample diluted to a predetermined concentration.

Available prior art acknowledge several devices and methods with variable technical features which describe collection, dilution and dispensing of a liquid specimen. Moreover, prior art do also recognize many multi-chamber sampling devices for swab sampling, comprising diverse technical solutions to perforate the membrane or alike between the chambers.

U.S. Pat. No. 3,233,785 describes a very basic and simple rinsing pipette, wherein a blood sample flows upwardly in a capillary by capillary attraction and automatically stops when reaching a chamber substantially wider in diameter than the capillary passage.

U.S. Pat. No. 3,453,941 discloses an apparatus for determining the blood group of a specimen comprising means for collecting, reagent availability in a container, mixing means and means to deposit the sample to a viewing plate.

An apparatus for taking multiple samples of biological liquid is described in U.S. Pat. No. 3,848,581. The document discloses an apparatus where the blood sample moves in a main canal which branches into individual test tubes which may contain appropriate reagents.

A diluter which provide for the aspiration of a predetermined quantity of a sample liquid followed by discharge of the sample together with a predetermined quantity of diluent is disclosed in U.S. Pat. No. 3,869,068.

U.S. Pat. No. 4,003,262 discloses an apparatus for measuring precise micro quantities of fluid samples wherein the self-filling capillary tube is open to atmosphere through an opening in the closed end of the shield.

A device for collecting, separating and dispensing non-pressurized liquids having a vent passageway exhausting air when liquid is drawn in, is taught in U.S. Pat. No. 4,136,036.

U.S. Pat. No. 4,396,024 discloses a device for extraction of capillary blood, a holder integrally connected thereto and a closure pin at the rear end of the capillary.

Another type of a sampling device is disclosed in U.S. Pat. No. 4,589,421 wherein the invention allows sampling without mechanical movement and dispensing of a precise amount of sample by means of mechanical movement. The sampling device as disclosed in U.S. Pat. No. 4,589,421 may also be an integral part of the test device.

Moreover, U.S. Pat. No. 4,690,005 discloses a dosage device by means of which it is possible to take a sample out of a liquid to mix the sample into a dilution liquid, e.g. a reagent, in a precise proportion, and to dose the mixture into another vessel e.g. a test tube or measurement vessel.

The invention of U.S. Pat. No. 5,833,630 relates to a sample collection device to collect capillary blood. In said invention the sample is absorbed by capillary action of a capillary positioned into a holder producing a closure means of a reagent liquid containing cuvette into which the sample is transferred for analyzes. A protective and pressure cap can be applied to the free end of the capillary. A downward movement of the pressure cap releases the sample into the cuvette, thereafter the sample is conveyed to the analyzer.

A further invention disclosing a method and kit for collecting samples of liquid specimens for analytical testing is disclosed in U.S. Pat. No. 5,935,864 wherein said method comprises a sample container and a reagent vial. The sample and the reagent in the reagent vial are drawn by capillary attraction into the chamber containing a test strip.

A sample means and system for testing a sample liquid disclosing the same principle as in U.S. Pat. No. 5,935,864 is disclosed in US 2005/0145046. Said US application provides a sampling means with a reservoir for a dilution liquid and/or reaction liquid. The method enables delivery of sample liquid and the dilution and/or reaction liquid in succession or at the same time, especially by a single actuation of the sampling means.

The invention of U.S. Pat. No. 6,803,021, B1 relates to a device for receiving and discharging a given amount of liquid. The sample is aspired by capillary attraction while the air escapes via an aperture. For discharging the liquid the aperture is closed and pressure is directed on the flexible bellows. U.S. Pat. No. 6,803,021 B1 further discloses an agitating means comprising a hook-like continuation which effectively stirs the liquid with a reagent in a test tube.

WO 2005/071388 discloses a sampling and assay device comprising a multi chamber assay format for swab sampling wherein needed reagents and liquid medium is available in said chambers of the assay device. The chambers are separated from each other by membranes which are punctured either by the sampling swab or a puncturing means. When applying a puncturing means the membranes are ruptured by relative movement of at least two parts of the assay device.

Accordingly, it is an aim of the present invention to provide a sampling device and method for volumetric collecting, volumetric diluting, mixing and dispensing liquids for further analytical testing. More specifically the present invention provides a volumetric dilution of a volumetric sample with a predetermined volume of e.g. a buffer or fluid comprising one or more reagents or any other fluid followed by a volumetric dispensing and mixing of said sample-diluent composition wherein the level of volumetric dilution and dispensing is predetermined. By positioning the engagement means e.g. flange and fluke to a fixed predetermined position the volumetric dilution and the volumetric amount to be dispensed can be regulated.

According to the present invention there is provided a device for dispensing a sample comprising:

a container comprising a sealed chamber bounded on at least one side by a penetrable member, a sampler defining a passage which is open at both ends, at least a portion of a passage extending from a first end comprising a capillary passage, the sampler comprising a penetrating means configured to penetrate said penetrable member such that said passage is in communication with said sealed chamber once said penetrable member has been penetrated.

Said container may be of any shape, preferably cylinder shaped, and size intended for clinical or hygiene tests. In the present disclosure the term container is defined to enclose any vessel e.g. test tube, vial or alike.

The capillary passage operates to draw samples into the capillary passage by capillary action. Once a sample has been taken the penetrating means can penetrate the penetrable member. As the sampler passes further into the sealed chamber the contents of the sealed chamber can be dispensed out of the sealed chamber and into the sampler. Simultaneously the sample will be dispensed out of the sampler, followed by, and mixed with, any liquid originally stored in the sealed chamber. Very efficient mixing can be performed by a vigorous vortex formed into the liquids which are dispended from the sampling device.

Accordingly, the invention comprises a device, method and kit wherein a penetrable member expels the content of the passage when operating as a piston. It expels the content of the passage either into the sealed chamber or the content of the sealed chamber out through said passage. Furthermore, the passage is emptied by expelling the content of the passage through the first end of the passage.

According to an embodiment of the invention the penetrable member is a puncturable member and the penetrating means comprises a puncturing means. Thus, when the user wants to access the contents of the sealed chamber the puncturable member is punctured by the puncturing means. According to another embodiment of the invention the penetrable member comprises a member with an aperture, the penetrating means comprising a plug which is arranged to seal the aperture. When the user wants to access the contents of the sealed chamber the penetrating means comprising the plug is pushed through the aperture so the passage is in fluid communication with the sealed chamber. According to another embodiment of the invention the penetrable member comprises a member having an aperture, the device further comprising a plug which is arranged to seal the aperture. Thus the penetrating means pushes the plug through the aperture to access the contents of the sealed chamber.

The sampler may be configured to slide inside the container and may comprise a protrusion arranged to abut against the walls of the container and limit penetration of the sampler into the container. Once the sampler has penetrated further into the container the protrusion abuts against the container to prevent further penetration. The protrusion is preferably arranged at or near the first end of the sampler and can thus additionally be used to support or rest against an auxiliary vessel into which the sample may be dispensed.

The first end of the sampler may be inside the auxiliary vessel and form a closed system. This prevents the release of potentially infectious material from the apparatus. The first end of the sampler may be designed to tightly fit to the opening of the reaction vessel to prevent any leakage from either the device or auxiliary vessel. The auxiliary vessel may have the shape and function, but is not limited to, of a test tube, cuvette, cassette, lateral flow or flow through assay device.

Advantageously, the volume of the sample to be taken may be controlled by the volume of the capillary passage. At the end of the capillary passage there may be a stepping zone in which the diameter of the hollow passage increases in a step wise fashion being ≥1.5 mm, usually 1 to 6 mm and preferably 2 to 3 mm. Thus the volume of liquid drawn is limited by the volume of the capillary passage. At the other end of the passage from the capillary passage the diameter of the passage is preferably greater than the capillary passage. Alternatively, a marked line on the capillary may be used to indicate the volume of the sample drawn into the capillary.

The sampler may comprise engagement means spaced apart from the second end of the sampler and configured to engage with the penetrable member after penetrating the penetrable member. The penetrable member may be movable and the engagement means configured to operate the penetrable member as a piston or plunger. The penetrable member thus moves simultaneously with the sampler as it penetrates further into the container. The volume of the sealed chamber thus decreases and any contained fluid is dispensed. To provide a good seal between the penetrable member and the sampler the penetrable member is preferably elastic.

To allow a sample to easily be drawn into the sampler at least one ventilation opening may be provided between the inside and outside of the container, the ventilation opening being arranged outside the sealed chamber. The ventilation means may conveniently be arranged in a flange configured to engage with the penetrable member after penetrating the penetrable member. The flange may contain at least one opening for ventilation. If the flange comprises several openings they are distributed either uniformly or irregularly through the flange. The opening may have any shape and size. Most preferably the opening is round having a diameter of 0.1 to 1.5 mm, preferably 0.2 to 0.3 mm. If located at the edge of the flange the shape of the opening may be half circled or alike.

The container may further comprise a second sealed chamber bounded on at least one side by a second penetrable member. The penetrating means will first penetrate the first penetrable member and the fluid contained in the first sealed chamber is dispensed. When the penetrating means is inserted further into the container and the second penetrable member penetrated the fluid contained in the second sealed chamber is dispensed.

The sampler may be configured to store dry reagents in the passage. The dry reagents are preferably stored within the non-capillary part of the passage. As the liquid from the sealed chamber is dispensed it thus automatically mixes with the dry reagents to form the required assay.

The invention relies on said penetrable member and a sampler comprising a penetrating means, at least one flange and/or at least one fluke and its counterpart. The invention relates to a penetrable member which is cylinder shaped and corresponds to a stopper which abuts the walls of said container and has a liquid and gas tight friction contact with said walls. When the sampler means comprising a penetrating means penetrates the elastic membrane of the penetrable member the flanges and flukes engage the sampler with said penetrable member which becomes a piston or plunger wherein the sampler comprises a shaft or rod of said piston. Said piston is movable back and forth inside the container enabling a positive or negative pressure in the fluid containing chamber. When the passage is open fluids can pass through the passage.

According to a further aspect of the invention there is provided a method of dispensing a sample using a device for dispensing a sample, the device comprising a container comprising a chamber bounded on at least one side by a penetrable member, said chamber comprising a fluid and said sampling device comprising a sampler comprising a capillary passage extending from a first end and a penetrating means at a second end and, said method comprising:

drawing a sample of fluid using said capillary passage; and penetrating said penetrable member to engage said penetrable member and operate said penetrable member as a piston.

An advantage of the present invention is to combine a capillary sampler and one or more additional reagents provided in one or more sealed chambers into one easily operational unit. Those additional reagents can be in solid, liquid and gas form.

Examples of specimen to be analysed are, but not limited to, blood, serum, plasma, saliva, urine, sputum, sweat, tears, cerebrospinal fluid and other body fluids of human or animal origin. Typical specimens are samples especially from open sites like blood drops from finger pricks, saliva from mouth, tears from eyes and open laboratory containers like test tubes. The fluid with which the sample is mixed is usually a buffer needed for the assay. The present invention enables simple mixing of the sample with assay reagents for further performance of chemical, biochemical or biomedical qualitative or quantitative assays. It is also possible to use the device for hygiene sampling of industrial water processing, dairy, beverages, cosmetics, determining hygiene of laboratory and surgical spaces and alike.

According to a further aspect of the invention there is provided a kit of parts comprising:

a container comprising a sealed chamber bounded on at least one side by a penetrable member; and a sampler defining a passage which is open at both ends, at least a portion of a passage extending from a first end comprising a capillary passage, the sampler comprising a penetrating means configured to penetrate said penetrable member such that said passage is in communication with said sealed chamber once said penetrable member has been penetrated.

According to the present invention the penetrable member and penetrating means of the kit device comprises a puncturable member and puncturing means, respectively. Alternatively said penetrable member may further comprise a member having an aperture and a plug, which may or may not form part of the penetrating means, arranged in the aperture. A kit of parts may further comprise an auxiliary vessel.

The invention will now be described with reference to the accompanying non-limiting drawings.

The present invention is designed to collect exact volumetric liquid samples, like blood, serum, plasma saliva, urine, sputum, sweat, tears, cerebrospinal fluid or other body fluids and liquids in open containers or any hygiene samples, and to dilute those samples and mix them with auxiliary reagents and finally dispense the obtained mixture to perform analytical tests, respectively.

As shown in FIGS. 1, 2, 3 and 4, the dispensing device comprises according to the invention a plurality of parts.

Figure 16:
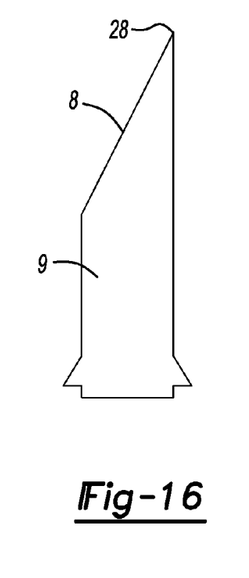
FIG. 16 illustrates an example of one alternative shape of one end of the sampler specially designed to puncture elastic materials.
Figure 17:
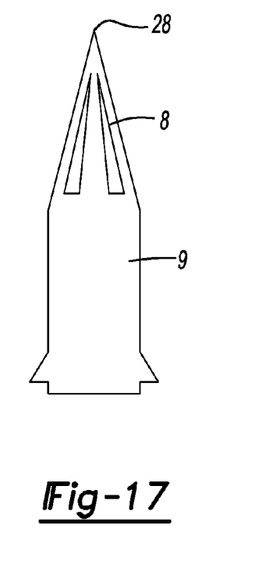
FIG. 17 illustrates an example of another alternative shape of one end of the sampler specially designed to puncture elastic materials.
Figure 18:
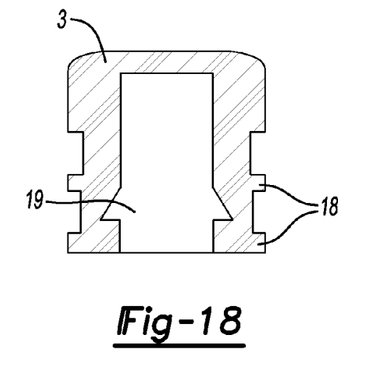
FIG. 18 illustrates an example of the cross-sectional view of one alternative shape of the first penetrable elastic member.
Figure 19:
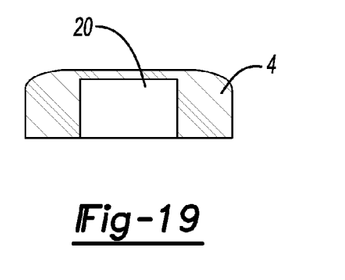
FIG. 19 illustrates an example of the cross-sectional view of one alternative shape of the second penetrable elastic member.

The first mechanical part is a sampler which constitutes sample collection and dispensing means which defines a passage open at both ends, the passage comprising a capillary tube or passage 27 extending along a portion of the passage. The capillary passage is a single hollow means allowing volumetric capillary passage between capillary opening 5 and stepping zone 6, only. Volumetric sampling of liquids takes place by capillary action and the dispensing of both liquids and gases takes place by using positive, preferably manual pressure. The stepping zone 6 allows passage of gases and liquids in both directions, however the stepping zone 6 stops the capillary action of the fluid when the inner diameter of 0.1 mm extends to ≥2.0 mm of the hollow construction e.g. the capillary gets larger by the clear cut step 7. Moreover, the dimensionally larger ≥1.5 mm (1 to 6 mm) end of the sampler comprises penetrating means, 9 with a single opening 8 or multiple openings as illustrated in FIGS. 16 and 17, respectively. In this embodiment the penetrating means form a sharp end or puncturing means, 9. FIG. 16 depicts a penetrating means in which the puncturing means is formed by the rim of the passage of the sampler. This puncturing means 9 is especially designed to efficiently puncture elastic materials while keeping the passage open for gases and liquids. Additionally, the sampler 1 which comprises the wider ≥1.5 mm (1 to 6 mm) hollow construction 10, which is substantially wider than the preceding narrow hollow construction (allowing capillary action) allows gases and liquids to pass through. This wide hollow construction 10 is specially designed to be a storage space for possible additional dry reagents 13 needed for the assay. This wide hollow construction 10 is located between the stepping zone 6 and the opening 8. Flanges 11, form engagement means and guide the movement of sampler 1 and act as an engagement means for the sampler 1 to move or change position inside the container 2. The flanges 11 are preferably circular or of sectorial or of any other form. The flukes 31 and its counterparts 32 of the sampler 1 are designed to catch the sampler 1 with penetrable member 3, hence forming one combined moving unit 1, 3. The sampler 1 and penetrable means 3 and 4 are caught by an engagement means further comprising a fluke 31 and its counterpart 32. Said engagement means is configured to operate the penetrable member as a piston by either pushing or pulling said penetrable member. The penetrable member is slidable within the container and the combined moving unit may thus act as a piston to expel contents of a chamber into the passage. Flanges 11 contain ventilation holes 14 which are needed for air or gas to escape during sampling and penetrating of the penetrable members 3, 4. Flange 11 guides and supports the movement of sampler 1 inside the container 2 during sampling and dispensing actions. Flange 11 is spaced apart from the end of the sample.

The fluke 31 and its counterpart may form a locking mechanism in which the sampler 1 may be unlocked from the penetrable member by twisting sampler 1 in one direction.

The container 2 forms a gas-and-liquid-tight cylinder and has contained in it one or more penetrable members. The penetrable members 3, 4 of the invention are elastic members which operate as stoppers. Penetrable member 3 is preferably cylinder shaped, wherein the walls of the penetrable member are against the wall of the container 2 and wherein one end of the penetrable member comprises a penetrable elastic membrane and wherein the other end is open. Said open end hides a sharp end of a penetrating means which is fixed to a shaft, wherein said penetrating means and shaft comprise at least one flange and at least one fluke which catch the shaft to the cylinder shaped penetrable member. The penetrable member becomes a piston when the shaft or rod comprising a penetrating means has been caught onto the penetrable member. When caught a back or forth movement is enabled creating either a positive or a negative pressure in a vessel comprising said penetrable member.

To allow passage of liquid or gas the penetrating means is hollow and forms part of the passage.

Figure 1:
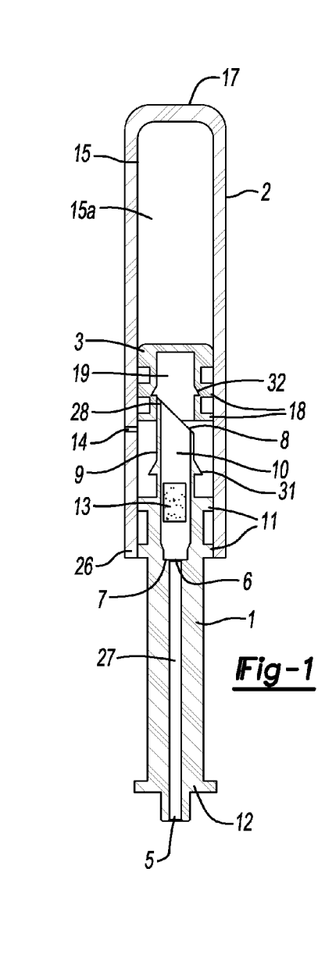
FIG. 1 is a schematic cross-sectional view of a preferred dispensing device comprising sampler and a container with one liquid reagent chamber inside the container and an opening for ventilation in the side wall of said container.
Figure 2:
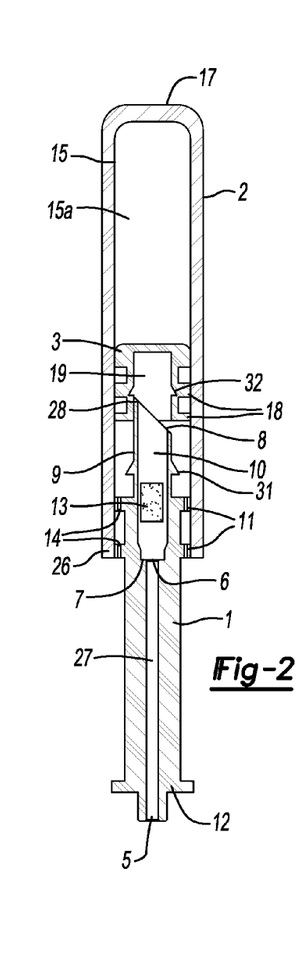
FIG. 2 is a schematic cross-sectional view of a preferred dispensing device with a liquid reagent chamber inside the container and openings for ventilation in the transaxial flange means of the sampler.
Figure 3:
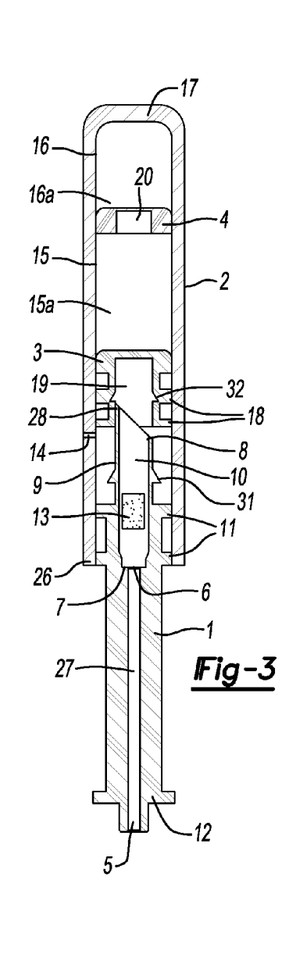
FIG. 3 is a schematic cross-sectional view of a preferred dispensing device with two liquid reagent chambers inside the container and an opening for ventilation in the side wall of said container.
Figure 4:
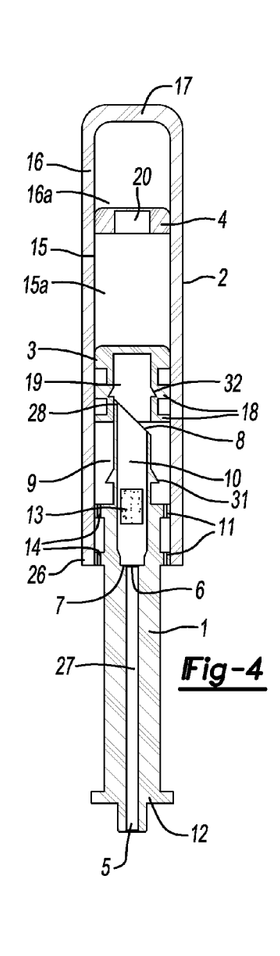
FIG. 4 is a schematic cross-sectional view of a preferred dispensing device with two liquid reagent chambers inside a container and openings for ventilation in the transaxial flange means of the sampler.

The container 2 constitutes a cylinder, which is open at the first (proximal) end 26 and closed at the second (distal) end 17. The container preferably has a uniform cross-section but is not limited to cylinders having a circular cross-section. The at least one opening 14 in the wall of the container 2 is an option for ventilation, escape and substitute, of air or gases between the external and internal spaces of the container 2. As described earlier, other options for ventilation are the ventilation holes 14 in the flange 11 of the sampler 1. The container 2 contains either one or more chambers, 15, 16 (also known as sealed chambers) forming volumetric compartments for storing the gas or liquid reagents 15a and 16a needed in analytical assays, respectively. These chambers are limited by the walls of the container 2, the closed second end 17 of the container 2 and the either the first penetrable member 3 (FIG. 1) or the first and second penetrable member 4 (FIG. 3). The penetrable members are puncturable by the sharp edge, 9 of the sampler and once punctured the sealed chamber is in communication with the passage. The non limiting example above discloses one chamber 15 or two chambers 15 and 16. This is an example only and it is understood that the spirit and scope of the present invention covers also a device comprising a plurality of chambers designed by a similar operational principle.

The penetrable members 3, 4 form elastic members which are puncturable by the sharp edge 9. As an example, a penetrable members 4 and its use is illustrated in FIGS. 3, 4, 8, 9, 10 and 11, respectively. Once perforated by the sharp edge 9 and when brought into contact with flange 11, fluke 31 and its counterpart 32 the elastic member may act as a piston, stopper or plunger. After being punctured, the puncturable member forms a seal preferably with the sharp edge 9 of the sampler.

However, the penetrable member, as described above, is not limited to said embodiment. It may also comprise a member with an aperture, wherein the member is seal tight and prevents any leakage by the use of a plug. The advantage of a member with an aperture is that it enables the use of a blunt penetrating means. Moreover, it is easier to enter the chamber through a member with an aperture since the member will not stretch at penetration. Accordingly, the penetrating means does not necessarily comprise a sharp edge but the shape can be more or less blunt.

Figure 22:
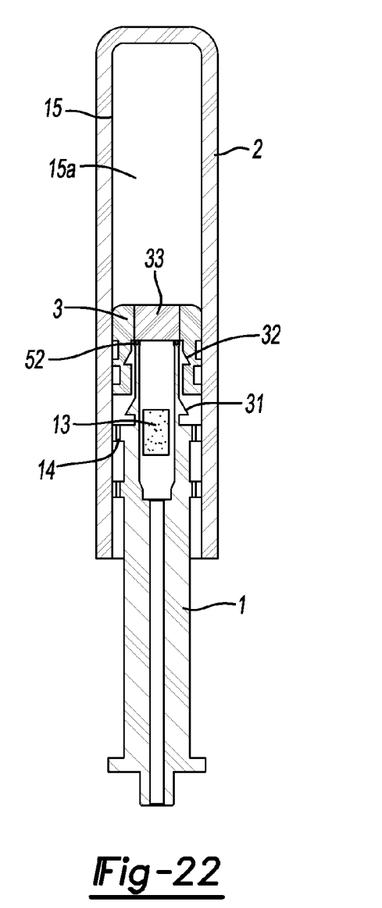
FIG. 22 is a schematic cross-sectional view of an alternative dispensing device in which the penetrable member has an aperture. The second end of the sampler comprises a liquid tight plug arranged inside the aperture of the penetrable member.
Figure 23:
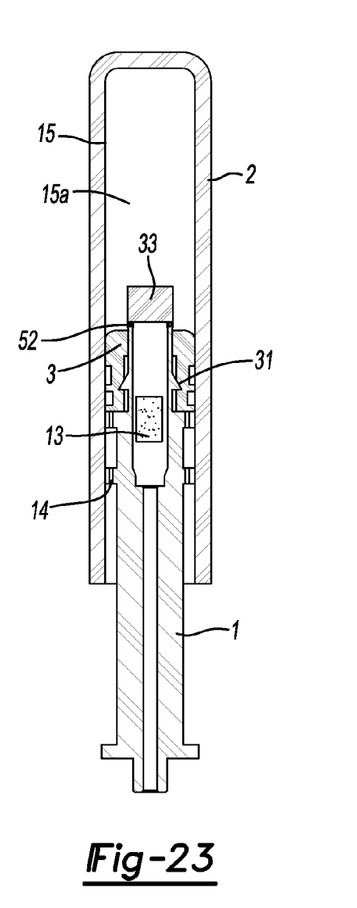
FIG. 23 illustrates the operation of the dispensing means of FIG. 22.

An additional embodiment of the invention is illustrated in detail in FIGS. 22 and 23. In this embodiment a plug 33 forms the penetrating means and the penetrable elastic member 3 comprises an aperture or opening which is liquid tight and seal tight plugged by plug 33. In this application liquid or gas reagents 15a of the closed volumetric chamber 15 passes to the passage through the openings 52 located in the side wall of the sampler 1. The passage is in fluid communication with the sealed chamber when the plug 33 is pushed into the volumetric chamber 15 containing either liquid reagent or gas 15a by means of an opposite movement of container 2 and the sampler.

In said additional embodiment the sampler comprises at least one opening 52 at the second end of the sampler such that the sampler defines a passage between the first end and the second end of the sampler. The plug 33 is leakage tight and seal tight by friction contact with the penetrable member 3. When the container 2 is pressed downwards towards the sampler the plug is pushed through the aperture and the passage into the chamber is opened through openings 52.

With some modifications the described second embodiment is also applicable to a sample collection and dispensing device comprising more than one chamber. Said modifications can be achieved for example by exploiting the learning of the present invention e.g. by arranging an additional plug in an aperture of the additional penetrable member.

Moreover, in further embodiment the plug does not form part of the penetrating means. The plug is arranged in the aperture of the penetrable member and the penetrating means are used to push the plug through the aperture. When the container 2 and sampler 1 are moved in opposite directions the edge of the penetrating means pushes the plug 33 into the chamber 15. The density of plug 33 can be chosen to be smaller than that of the fluid 15a in the chamber 15 enabling the plug 33 to float away from the aperture 8 and, accordingly, allow the passage of the sampler to be in fluid communication with the sealed chamber.

The penetrable members 3 and 4 limit and determine the volume of chambers 15 and 16 in relation to each other and also in combination with the walls and closed second (distal) end 17 of the container 2. The penetrable members 3 and 4 act as stationary stoppers during storage of reagent containing medium, gases or liquids in said chamber. The distal end 28 of the sharp end 9 of the sampler 1 rests inside the penetrable members 3 in space 19, especially designed for free escape of air or gases from the capillary tube 27 of the sampler 1 during sampling. However, when an external force is applied to the container, the distal end 28 of the sharp end 9 of the sampler 1 penetrates the penetrable members 3 and 4 forcing them to move as plungers/pistons 3 and 4. In addition to penetration of the penetrable members 3 and 4 with the distal end 28 of the sharp end 9 of the sampler 1, fluke 31 catches its counterpart 32 and flange 11 engages penetrable member 3 to form an engagement means of the sampler 1. Pressure is applied to the sampler 1 and this movement drains reagent medium, gases and/or liquids volumetrically from chambers 15 and 16. An exact volumetric amount of said gases or liquids which is dispensed out from device is determined by the length of the movement of said penetrable members 3 and 4 inside the predetermined chambers 15 and 16 of said container 2. Hence, it is possible to overfill said chambers 15 and 16 of said container 2 with reagents and dispense out smaller exact predetermined volumes of said reagents regulated by the location of, for example stopper 12. This helps in controlling the possible evaporation of gases and liquids out from chambers 15 and 16 of said container 2 during long storage of said reagents and also in accuracy requirements of dosing said reagents into said chambers 15 and 16. An opposite flow is also possible if negative force and pressure is applied.

The device of the present invention comprises features wherein the volumetric sample is obtained by the sampler comprising a capillary tube with one open end 5 for sampling and another end comprising a stepping zone 6 which is wider than the diameter of the capillary. The capillary action ceases when the sample reaches the stepping zone.

The volumetric dilution and dispensing of the sample rely on diluting the sample with a predetermined volume of liquid and dispensing of a predetermined volume of said sample-fluid composition. Said device of the present invention is disclosed in detail elsewhere in the specification. The device comprises a sampler 1, at least one penetrable member 3 which preferably is a cylinder shaped stopper with one open end comprising a preferably central passage and one closed end, one or more protruding flanges 11 and one or more flukes 31 positioned on the passage and fluke counterpart(s) 32 in the inner wall of the open end of the penetrable member.

The sampler 1 defines a passage which comprises a hollow construction 10 with a penetrating means 9. The flukes and their counterparts and the flanges and stopper are embodiments enabling volumetric dilution and volumetric dispensing. By selecting a proper positioning of fluke(s) and/or flange(s) and/or stopper the dilution of the sample can be regulated according to the needs and to equal with a predetermined diluent volume. Similarly, the volumetric volume to be dispensed may be regulated by the same features i.e. by choosing the proper positioning of the fluke(s), flange(s) and stopper and, accordingly, the position at which they catch. Advantageously, said proper positioning may be fixed according to needs.

The advantage of a regulated dilution is that the chamber(s) can be overfilled with diluent to avoid that the loss of diluent due to evaporation during storage will disable the assay. Said feature extends the shelf life of the device.

An efficient mixing of the sample and the reagents can also be performed by using negative pressure for passing the sample into the chamber. This action is followed by the use of positive pressure, which forces the sample and the reagent mixture out of the device through the sampler. Also several back and forth movements of the liquid can be used in order to facilitate the mixing of different reaction components.

Figures 5, 6:
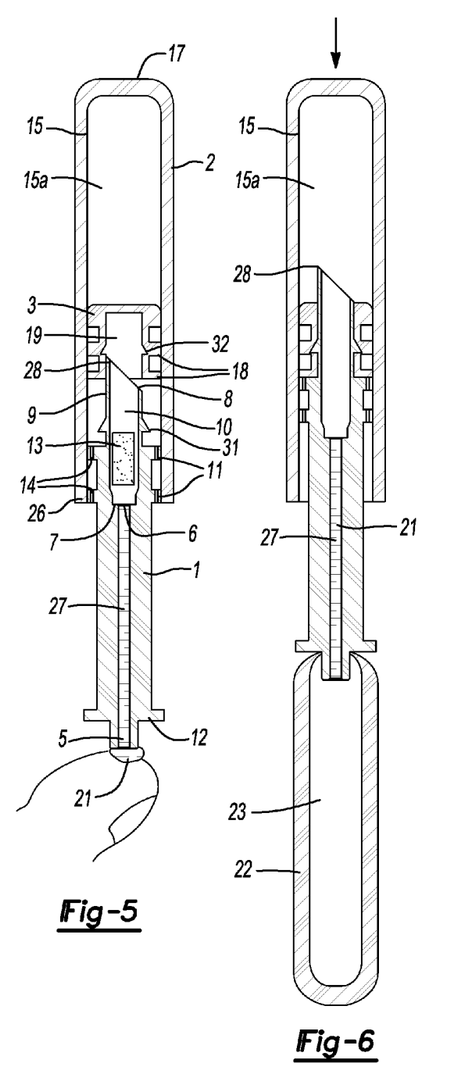
FIG. 5 illustrates the use of the dispensing device of FIG. 2 to collect a blood sample from a finger tip.
FIG. 6 illustrates the combination of the dispensing device of FIG. 5 and an auxiliary reaction vessel.
Figure 7:
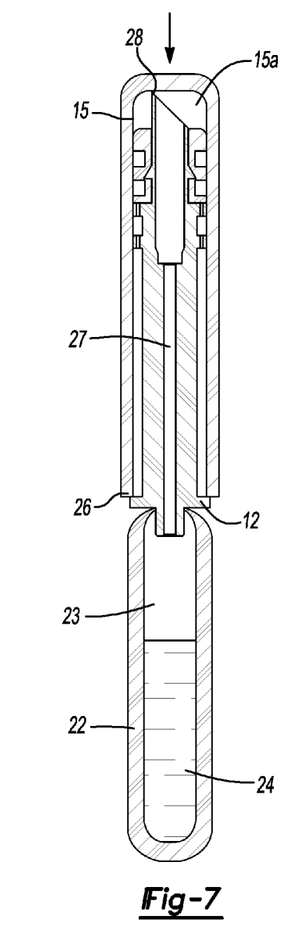
FIG. 7 illustrates mixing and dispensing of a blood sample and dried reagents with the liquid reagents from the reagent chamber of the dispensing device of FIG. 6 into the auxiliary reaction vessel of FIG. 6.
Figure 8:
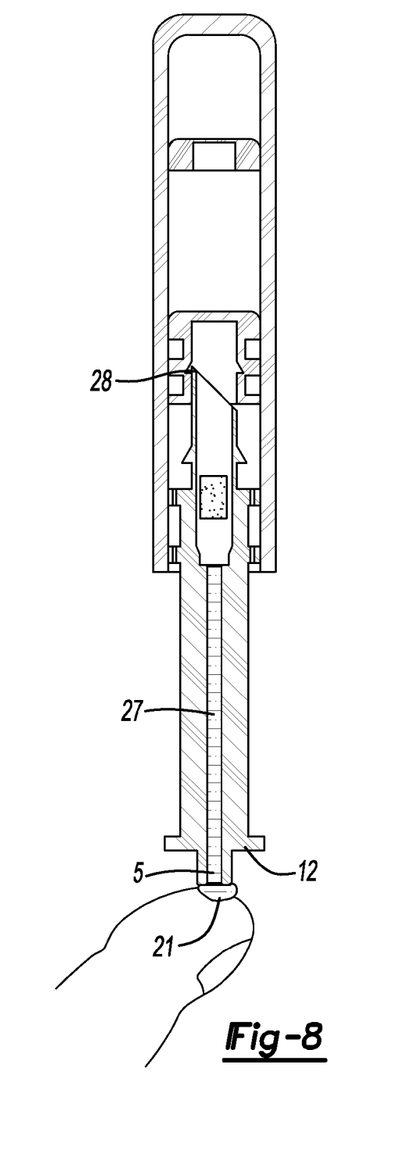
FIG. 8 illustrates the use of the sampler-dispenser device of FIG. 4 to collect a blood sample from a finger tip.

FIGS. 5-7 show schematically in cross-section the procedure for sampling, diluting, mixing and dispensing the sample 21, one or several dried reagent(s) 13 and a liquid reagent 15a. The reagent may comprise one or several reagent(s) or a reagent free buffer. According to the invention this can be achieved in only two simple sequential steps using a container containing one volumetric chamber 15. The first step collects the volumetric sample from a drop of whole blood 21 by using the capillary action between the opening 5 and stepping zone 6 of the sampler 1. Fluid movement in the capillary is stopped at the stepping zone 6, hence allowing the exact volumetric sampling. Typical sample volumes used are 0.1-100 µl, most typically 5-20 µl. Typical internal diameter of the capillary part between the opening 5 and stepping zone 6 of the sample collection and dispensing means 1 is 0.1 mm≥2.0 mm, preferably 0.1 mm-2 mm. The inner dimension of the stepping zone immediately after the capillary means may be of about the external dimension of approximately 0.3 to 3 mm of the capillary means. The length of the capillary means is dependent on the predetermined volume of the sample and the internal dimension of said capillary means. The air pressure is kept in equilibrium between external and internal environment of the sampler by allowing air to escape from between the sampler and penetrable member through ventilation openings 14 when the sample 21 moves from opening 5 to the stepping zone 6, where the capillary action ceases. The capillary arrangement results in a very accurate and reproducible sample volume FIG. 5.

The container 2 is configured such that the sampler may slide easily within the cylinder shaped container. The sampler may comprise a protrusion, or stopper, 12 which abuts against the container to limit penetration of the sampler into the container. The stopper 12 is preferably of circular or sectorial form, although it is not limited to these forms. In FIG. 6 the second step is shown wherein the container 2 is pressed downwards while stopper 12 of the sample collection and dispensing means 1 rests on the upper part of an auxiliary reaction vessel 22. The auxiliary vessel 22 may have the shape and function, but is not limited to, of a test tube, cuvette, cassette or lateral flow or flow through assay device. The auxiliary vessel 22 rests against the stopper 12 of the sampler 1. The opening 5 of the sampler 1 is located in the internal space 23 of auxiliary vessel 22. The downwardly directed mechanical force applied on the closed end 17 of the container 2 causes the penetration of the penetrable member 3 by the distal end 28 of the sharp end 9 of the sampler 1. The catching of the sampler 1 with the penetrable member 3 takes place during penetration, hence forming a plunger-unit with a hollow connecting rod. Puncturing of penetrable member 3 accomplishes passage from the liquid reagent chamber 15, through the opening 8 at the sharp end 9 and the wide hollow means 10 containing the dried reagents 13 further through the stepping zone 6 and finally through capillary tube 27 and opening 5 into the internal part 23 of the reaction vessel 22.

FIG. 7 illustrates complete dispensing achieved when further force is applied on the closed (distal) end 17 of the container 2. The container 2, the joined sampler 1, (caught by fluke 31 and its counterpart 32 of the penetrable member 3) and penetrable member 3 move in friction contact within each other in opposite directions and stop when stopper 12 abuts against the open end 26 of container 2. This action forces the liquid reagent 15a out from the chamber 15 through formed open passage, hence flushing and mixing the dried reagents 13 from the wide hollow construction 10 and, furthermore, forces the sample out through the capillary sampling channel 27 into the internal space 23 of the auxiliary vessel 22. The final ready-to-measure mixture 24 comprises sample 21, dried reagents 13 and reagent liquid 15a.

FIGS. 8-11 illustrate in cross-section the procedure for sampling, diluting, mixing and dispensing the sample 21, dried reagents 13 and two liquid reagents 15a and 16a. The first reagent is stored in sealed chamber 15 and the second reagent in a second sealed chamber 16 bounded by another elastic member and arranged in series with the first sealed chamber. The procedure is performed in three sequential steps using a device comprising two separate sealed chambers 15, 16. The first step collects the volumetric sample from a drop of whole blood 21 by using the capillary action between the opening 5 and stepping zone 6 of the sampler 1. Fluid movement in the capillary is stopped at the stepping zone 6, hence allowing an exact volumetric sampling. Typical sample volumes used are 0.1-100 µl, most typically 5-20 µl. Typical internal diameter of the capillary part between the opening 5 and stepping zone 6 of the sample collection and dispensing means 1 is 0.1 mm>2 mm. The air pressure is kept in equilibrium between external and internal environment of the sampler-dispenser device by allowing air to escape through ventilation openings 14 when the sample 21 moves from opening 5 to the stepping zone 6, where the capillary action ceases. The capillary arrangement results in a very accurate and reproducible sample volume FIG. 8.

Figure 9:
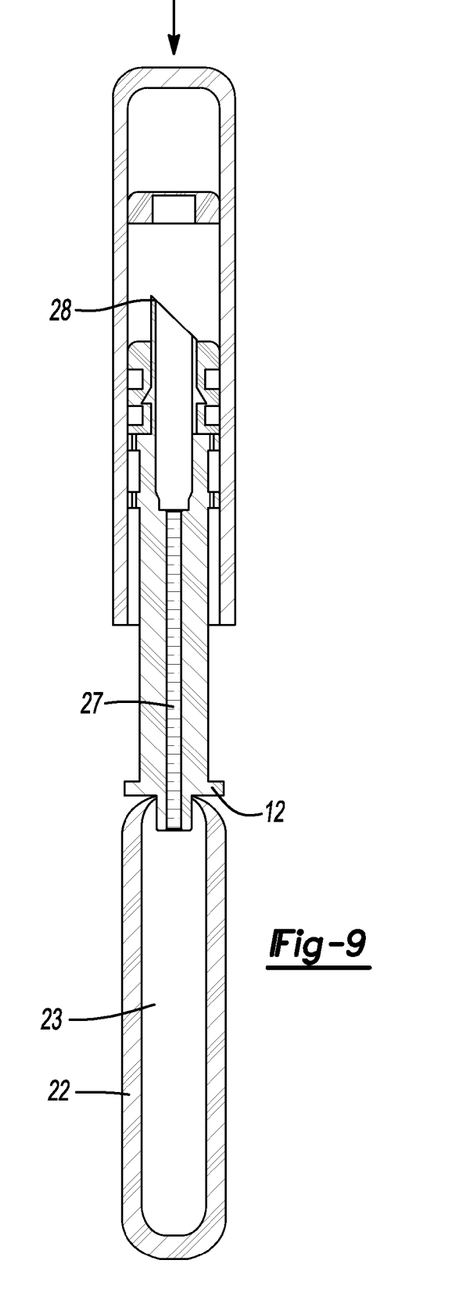
FIG. 9 illustrates the combination of the dispensing device of FIG. 8 and an auxiliary vessel.

In FIG. 9 the second step is shown wherein the container 2 is pressed downwards while stopper 12 of the sample collection and dispensing means 1 rest on the upper part of an auxiliary reaction vessel 23. The opening 5 of the sampler 1 is located in the internal space 23 of reaction vessel 22. The downwardly directed mechanical force applied on the closed end 17 of the container 2 causes the penetration of the penetrable member 3 by the distal end 28 of the sharp end 9 of the sampler 1. The catching of the sampler 1 and penetrable member 3 by fluke 31 take place during penetration, hence forming a plunger-unit with a hollow connecting rod. Penetration of the penetrable member 3 accomplishes passage from the liquid reagent chamber 15 through the opening 8 at the sharp end 9 and the wide hollow means 10 containing the dried reagents 13 further through the stepping zone 6 and finally through capillary tube 27 and opening 5 into the internal space 23 of the auxiliary vessel 22. When further force is applied on the closed end 17 of container 2 the container 2 and the sampler 1 caught with the penetrable member 3 move in friction contact within each other in opposite directions forcing the liquid reagent 15a out from the chamber 15 through the formed open passage, thus flushing and mixing the dried reagents 13 from the wide hollow construction 10 and also forcing the sample 21 through the capillary tube 27 into the internal space 23 of the auxiliary vessel 22. This movement continues (FIG. 10) until the distal end 28 of the sharp end 9 of the sampler 1 contacts the second penetrable member 4. An extended further force downwards causes the distal end 28 of the sharp end 9 of the sampler 1 to penetrate the second penetrable member 4.

Sampler 1 may catch second penetrable member 4 by at least one additional fluke at the more distal end of sampler 1, and its counterpart in the second penetrable member 4. The additional fluke 31 of sampler 1 and its counterpart 32 of the second penetrable member 4 have different angular positions from the first fluke 31 and its counterpart 32. Different angular positioning of subsequent flukes and counterparts can be exploited when additional sealed chambers are introduced into container 2. Alternatively, by varying the size or shape of flukes and their counterparts from those of other fluke-counterpart pairs it is possible to determine when and which fluke-counterpart pair should catch each other. Moreover, the axial positioning of additional flukes of sampler 1 may be such that the second penetrable member 4 will be in either close contact with or apart from the first penetrable member 3. Accordingly, the exact position of every additional penetrable member can be adjusted. However, usually the first penetrable member is caught by a fluke and this is sufficient to perform the function of operating as a piston according to the present invention and additional penetrable members are not caught by sampler 1. Accordingly, when the additional penetrable member has been penetrated it is pushed upwards in the container 2 by sampler 1 and reaches the distal end of container 2, where it sticks to the closed end 17 of container 2 by friction contact.

Figures 10, 11:
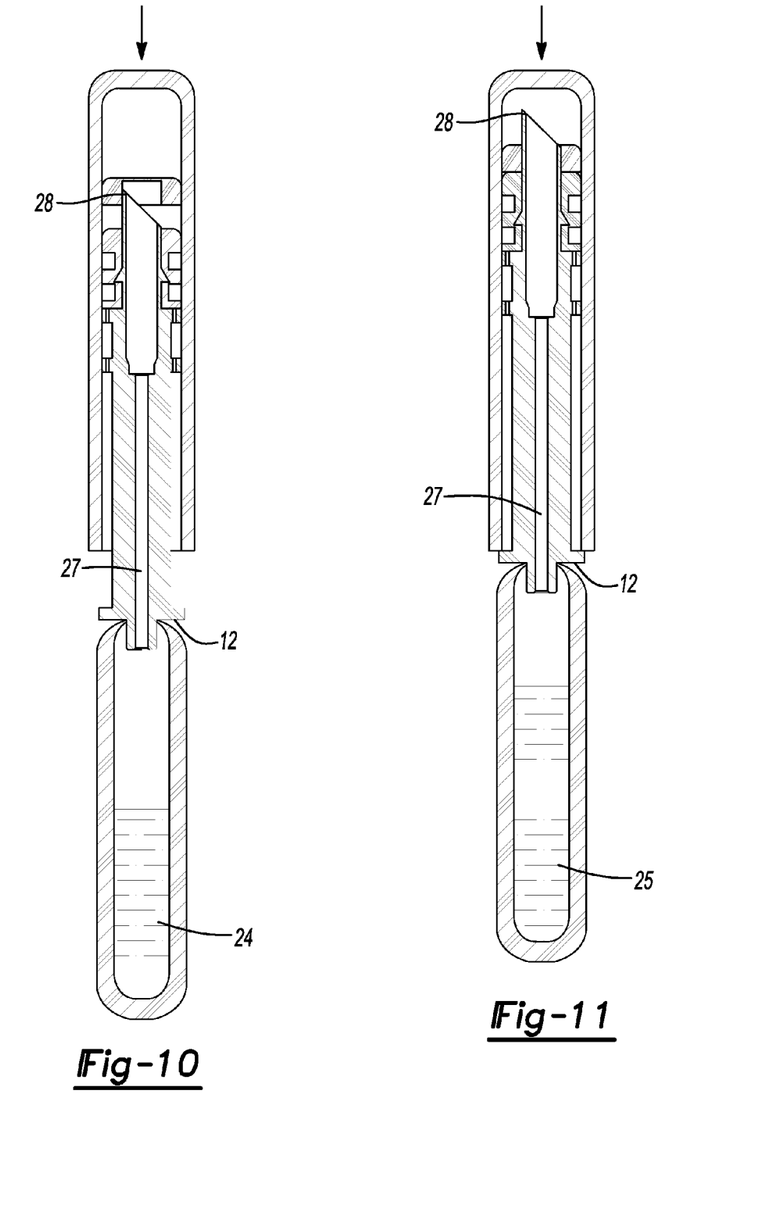
FIG. 10 illustrates mixing and dispensing of a blood sample and dried reagents with the liquid reagents from the first reagent chamber of the dispensing device of FIG. 9 into the auxiliary vessel of FIG. 9.
FIG. 11 illustrates mixing and dispensing of additional reagents from the second reagent chamber of the dispensing device of FIG. 10 into the auxiliary vessel of FIG. 10.
Figure 12:
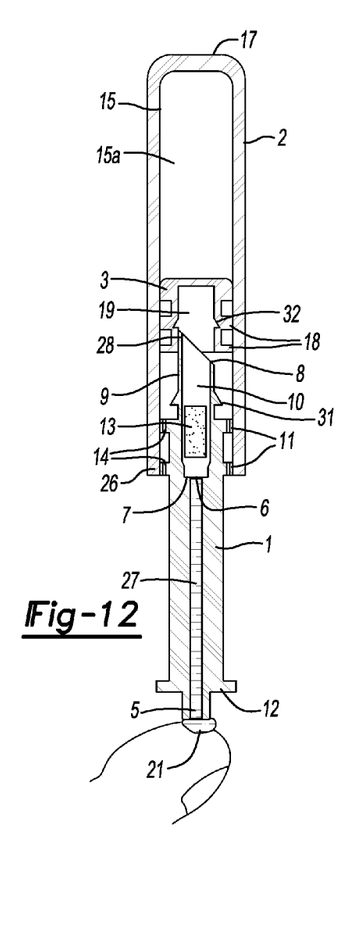
FIG. 12 illustrates the use of the dispensing device of FIG. 2 to collect a blood sample from a finger tip.
Figure 13:
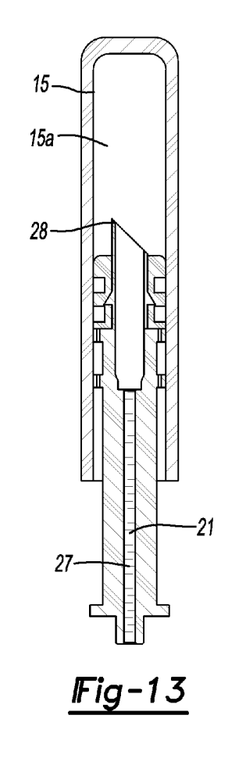
FIG. 13 illustrates the dispensing device of FIG. 12 containing the capillary part filled with the sample and the penetrating means which has penetrated the first penetrable member and entered the first fluid containing sealed chamber.
Figure 14:
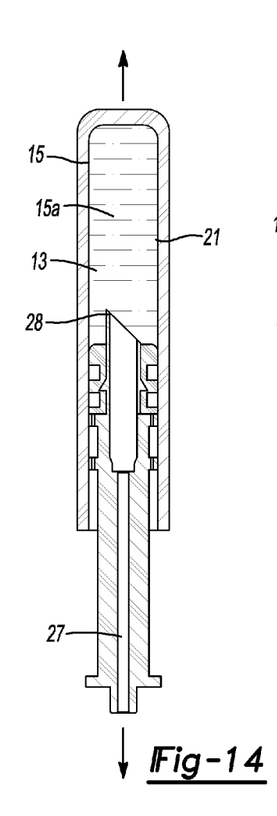
FIG. 14 illustrates the dispensing device of FIG. 13 where opposite forces and travel are performed between the sampler and the container of sampling device for generating a negative pressure inside the sealed chamber for transferring the sample from the capillary part of the sampler into the first sealed chamber.
Figure 15:
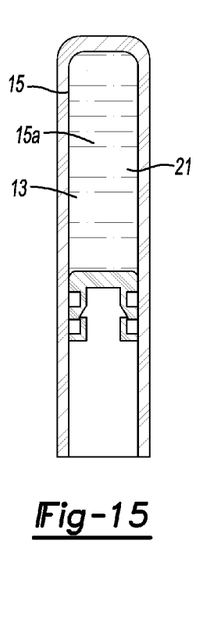
FIG. 15 illustrates the sealed chamber of dispensing device containing the sample and the reagents.

FIG. 11 illustrates further how the downwardly directed opposite movement of the sampler 1 and stopper/plunger/piston means 3 and 4 inside the container 2 forces the liquid reagent 16a out from chamber 16 through the formed open passage. The liquid reagent 16a from chamber 16 becomes mixed in the internal space 23 of the reaction vessel 22 with the liquid reagent 15a originating from the first chamber 15, the dried reagents 13 originating from the wide hollow construction 10 and the sample 21 originating from the capillary sampling tube. The opposite movement of the sampler 1, penetrable members 3 and 4 and the container 2 continues until the open end 26 of the container 2 contacts stopper 12 resulting in cessation of the outflow and mixing of sample and reagents. The final ready-to-measure mixture 24 comprises sample 21, dried reagents 13 and reagent liquids 15a and 16a.

Figure 20:
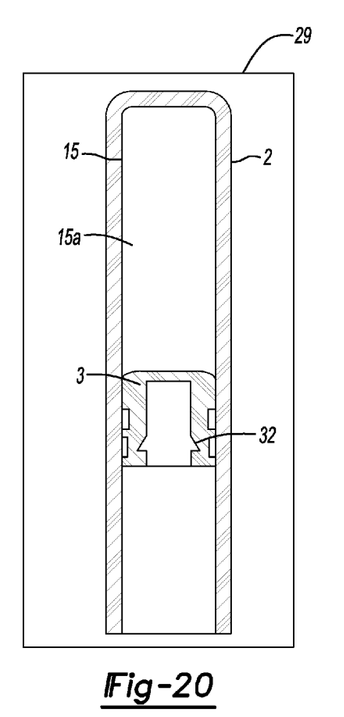
FIG. 20 illustrates a package comprising the combination of a container, the elastic penetrable member of cylinder shape and one sealed chamber containing the gaseous or liquid reagent needed in analytical assays. Optionally, there may be more than one sealed chamber.

FIG. 20 illustrates the combination of a container 2, the penetrable member 3 and one volumetric chamber 15 containing the gaseous or liquid reagent 15a needed in analytical assays in a package to be later combined to the sampler 1 shown in FIG. 21. Optionally, container 2 of the device may comprise two or more chambers.

Figure 21:
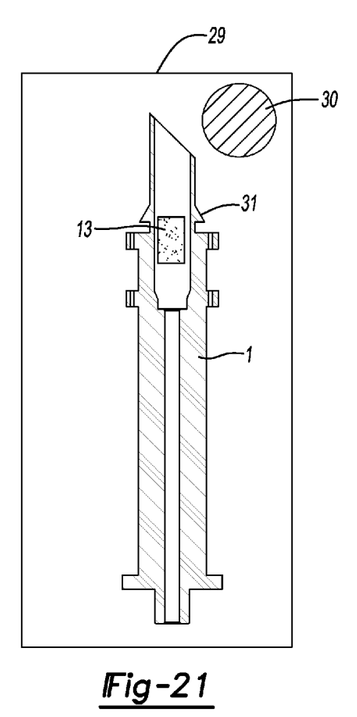
FIG. 21 illustrates a dry package comprising the sampler.

FIG. 21 illustrates the sampler 1 in optimal setting with dry reagents 13 in a dry package 29 with a desiccant like silica gel 30 to be later combined to the device shown in FIG. 20 comprising the container 2, the penetrable member 3 and one or more chambers 15 and/or 16 containing the gaseous or liquid reagents 15a and/or 16a needed in analytical assays.

As mentioned above these two clearly distinct part of the device which are described in FIGS. 20 and 21, respectively, are combined into one functional unit according to the present invention to enable sampling, diluting, mixing and dispensing as described.

The invention claimed is:

1. A device comprising:
   a container comprising an open end and a closed end;
   a first penetrable member disposed within said container and cooperating with said container to form a first sealed chamber, said first penetrable member is movable within said container and operable as a piston within said container;

a sampler defining a passage for sampling a sample which is open at first and second ends, at least a portion of said passage extending from said first end comprising a capillary passage operable to draw said sample into said passage by capillary action, said sampler being movable relative to said container, said sampler comprising a penetrating means configured to penetrate said first penetrable member such that said passage is in communication with said first sealed chamber once said penetrable member has been penetrated.

2. The device according to claim 1 wherein said first penetrable member comprises a puncturable member and said penetrating means comprises a puncturing means configured to puncture said puncturable member.

3. The device according to claim 1 wherein said first penetrable member comprises a member having an aperture and said penetrating means comprises a plug, said plug being arranged to seal said aperture, wherein said plug is disposed at a distal end of said penetrating means such that moving said penetrating means into said penetrable member moves said plug into said chamber.

4. The device according to claim 1 wherein said first penetrable member comprises a member having an aperture extending entirely therethrough, the device further comprising a plug, said plug being arranged to seal said aperture, said penetrating means pushing said plug through said aperture and into said chamber.

5. The device according to claim 1 wherein said sampler is configured to slide inside said container.

6. The device according to claim 5 wherein said sampler comprises a protrusion configured to abut against said container and arranged to limit movement of said sampler into said container after moving said sampler into said container.

7. The device according to claim 5, wherein said sampler comprises a shaft or rod.

8. The device according to claim 1 wherein said sampler comprises an engagement means configured to engage with said penetrable member after said penetrating means penetrates said penetrable member.

9. The device according to claim 8 wherein said container is a cylinder in which said first penetrable member is slidable, said engagement means being configured to engage said first penetrable member to operate said first penetrable member as said piston.

10. The device according to claim 9 wherein said first penetrable member is operable to expel contents of said passage.

11. The device according to claim 10 wherein said first penetrable member is operable to expel said contents of said passage into said first sealed chamber.

12. The device according to claim 10 wherein said first penetrable member is operable to expel said contents of said passage from said first end.

13. The device according to claim 9 wherein said first penetrable member is operable to expel contents of said first sealed chamber through said passage.

14. The device according to claim 8 wherein said engagement means is spaced apart from said second end of said passage.

15. The device according to claim 8 wherein said engagement means is configured to operate said first penetrable member as said piston by pushing said first penetrable member.

16. The device according to claim 8 wherein said engagement means comprises a locking means configured to lock with said first penetrable member.

17. The device according to claim 16 wherein said locking means comprises a fluke, said first penetrable member being configured such that said sampler is unlocked from said first penetrable member by twisting.

18. The device according to claim 8 wherein said engagement means comprises a flange.

19. The device according to claim 8 wherein said engagement means comprises a catching means configured such that said catching means catches said penetrable member.

20. The device according to claim 19 wherein said catching means is configured to operate said first penetrable member as said piston by pulling said first penetrable member.

21. The device according to claim 19 wherein said catching means comprises a fluke.

22. The device according to claim 1 wherein a diameter of a portion of said passage extending from said second end of said passage is larger than a diameter of said capillary passage.

23. The device according to claim 1 wherein, adjacent to said capillary passage, a diameter of said hollow passage increases in a step fashion.

24. The device according to claim 1 wherein said first penetrable member is elastic and an end of said sampler is configured to form a seal with said first penetrable member after penetrating said first penetrable member.

25. The device according to claim 1, further comprising at least one ventilation opening disposed between an inside and an outside of said container and arranged to vent a space between said sampler and said first penetrable member.

26. The device according to claim 25 wherein said sampler comprises a flange spaced apart from an end of said sampler and configured to engage with said first penetrable member after said penetrating means penetrates said first penetrable member, said ventilation opening being arranged in said flange.

27. The device according to claim 1 further comprising a second sealed chamber bounded on at least one side by at least a second penetrable member configured to be penetrated by said penetrating means, said second sealed chamber being arranged in series with said first sealed chamber.

28. The device according to claim 1 wherein said penetrating means is formed by a rim of said passage.

29. The device according to claim 1 wherein said first penetrable member is formed in the shape of a cylinder having a closed end, an open end, and a wall arranged to abut against a wall of said container to allow said sampler to enter said first penetrable member through said open end.

30. The device according to claim 1 wherein said sampler stores dry reagents in said passage.

31. The device according to claim 1 wherein said first sealed chamber contains a reagent.

32. The device according to claim 1 wherein said device is a volumetric sampling and volumetric dispensing device.

33. The device according to claim 1 wherein said first sealed chamber contains a liquid.

34. The device according to claim 1 further comprising an auxiliary vessel.

35. The device according to claim 34 wherein said auxiliary vessel comprises one of a test tube, a cuvette, a cassette, a lateral-flow assay device, and a flow-through assay device.

36. A method of drawing and dispensing a sample using a device for drawing and dispensing said sample, the device comprising a container comprising a chamber bounded on at least one side by a penetrable member, said chamber comprising a fluid and said device comprising a sampler comprising a capillary passage extending from a first end of the sampler and a penetrating means at a second end of the sampler and, said method comprising: drawing a sample of fluid by capillary action using said capillary passage; and penetrating said penetrable member to engage said penetrable member and operate said penetrable member as a piston, wherein said piston is operated to expel said sample of fluid through said capillary passage.

37. The method according to claim 36 wherein said penetrable member comprises a puncturable member and said penetrating means comprises a puncturing means which punctures said puncturable member.

38. The method according to claim 36 wherein said penetrable member comprises a member having an aperture and said penetrating means comprises a plug, said plug being arranged to seal said aperture, wherein said plug is disposed at a distal end of said penetrating means such that moving said penetrating means into said penetrable member moves said plug into said chamber.

39. The method according to claim 36 wherein said penetrable member comprises a member having an aperture extending entirely therethrough, said device further comprising a plug, said plug being arranged to seal said aperture, said penetrating means pushing said plug through said aperture and into said chamber.

40. The method according to claim 36 wherein said sample comprises bodily fluids.

41. The method according to claim 40 wherein said bodily fluids comprise blood.

42. The method according to claim 36 wherein said fluid comprises a hygiene sample.

43. The method according to claim 36 wherein said piston is operated to expel said sample of fluid into said chamber.

44. The method according to claim 43 wherein said method further comprises: mixing said sample with said fluid in said chamber; and expelling said combined sample and fluid through said passage.

45. The method according to claim 36 wherein said fluid is expelled into an auxiliary vessel.

46. The method according to claim 36, further comprising at least one ventilation opening disposed between an inside and an outside of said container and arranged to vent a space between said sampler and said penetrable member.

47. The method according to claim 46 wherein said sampler comprises a flange spaced apart from an end of said sampler and configured to engage with said penetrable member after said penetrating means penetrates said penetrable member, said ventilation opening being arranged in said flange.

48. A kit of parts comprising: a container comprising a sealed chamber bounded on at least one side by a penetrable member operable as a piston within said chamber; and a sampler defining a passage which is open at both ends, at least a portion of a passage extending from a first end comprising a capillary passage operable to draw a sample of fluid into said passage by capillary action, the sampler comprising a penetrating means configured to penetrate said penetrable member such that said passage is in communication with said sealed chamber once said penetrable member has been penetrated.

49. The kit of parts according to claim 48 wherein said penetrable member comprises a puncturable member and said penetrating means comprises a puncturing means configured to puncture said puncturable member.

50. The kit of parts according to claim 48 wherein said penetrable member comprises a member having an aperture and said penetrating means comprises a plug, said plug being arranged to seal said aperture, wherein said plug is disposed at a distal end of said penetrating means such that moving said penetrating means into said penetrable member moves said plug into said chamber.

51. The kit of parts according to claim 48 wherein said penetrable member comprises a member having an aperture extending entirely therethrough, said device further comprising a plug, said plug being arranged to seal said aperture, said penetrating means pushing said plug through said aperture and into said chamber.

52. The kit of parts according to claim 48 further comprising an auxiliary vessel.

53. The kit of parts according to claim 48, wherein said penetrable member is movable relative to said sealed chamber and operable as a piston within said sealed chamber.

54. The kit of parts according to claim 48, further comprising at least one ventilation opening disposed between an inside and an outside of said container and arranged to vent a space between said sampler and said penetrable member.

55. The kit of parts according to claim 54 wherein said sampler comprises a flange spaced apart from an end of said sampler and configured to engage with said penetrable member after said penetrating means penetrates said penetrable member, said ventilation opening being arranged in said flange.

* * * * *